US008623062B2

(12) United States Patent
Kondrashov (10) Patent No.: US 8,623,062 B2
(45) Date of Patent: Jan. 7, 2014

(54) SYSTEM AND METHOD TO STABLIZE A SPINAL COLUMN INCLUDING A SPINOLAMINAR LOCKING PLATE

(76) Inventor: Dimitriy G. Kondrashov, San Francisco, CA (US)

(*) Notice: Subject to any disclaimer, the term of this patent is extended or adjusted under 35 U.S.C. 154(b) by 693 days.

(21) Appl. No.: 12/561,141

(22) Filed: Sep. 16, 2009

(65) Prior Publication Data

US 2010/0082067 A1 Apr. 1, 2010

Related U.S. Application Data

(60) Provisional application No. 61/194,516, filed on Sep. 29, 2008.

(51) Int. Cl.
*A61B 17/80* (2006.01)

(52) U.S. Cl.
USPC .......................................... 606/280; 606/246

(58) Field of Classification Search
USPC ................... 606/280, 70, 71, 281, 283–291, 606/246–250, 264–266
See application file for complete search history.

(56) References Cited

U.S. PATENT DOCUMENTS

| | | | |
|---|---|---|---|
| 5,127,912 A | 7/1992 | Ray et al. | |
| 5,300,073 A | 4/1994 | Ray et al. | |
| 5,397,363 A | 3/1995 | Gelbard | |
| 5,470,333 A | 11/1995 | Ray | |
| 5,531,746 A * | 7/1996 | Errico et al. | 606/287 |
| 5,531,747 A | 7/1996 | Ray | |
| 5,601,553 A | 2/1997 | Trebing et al. | |
| 5,603,713 A | 2/1997 | Aust et al. | |
| 5,667,507 A | 9/1997 | Corin et al. | |
| 5,676,703 A | 10/1997 | Gelbard | |
| 5,681,311 A | 10/1997 | Foley et al. | |
| 5,702,396 A | 12/1997 | Hoenig et al. | |
| 5,709,684 A | 1/1998 | Errico et al. | |
| 5,713,900 A | 2/1998 | Benzel et al. | |
| 5,752,955 A | 5/1998 | Errico | |
| 5,766,254 A | 6/1998 | Gelbard | |
| 6,036,693 A | 3/2000 | Yuan et al. | |
| 6,045,552 A | 4/2000 | Zucherman et al. | |
| 6,129,730 A | 10/2000 | Bono et al. | |
| 6,132,464 A | 10/2000 | Martin | |
| 6,139,550 A | 10/2000 | Michelson | |

(Continued)

FOREIGN PATENT DOCUMENTS

| | | |
|---|---|---|
| EP | 1852077 A2 | 11/2007 |
| JP | 2006212435 A | 8/2006 |

(Continued)

OTHER PUBLICATIONS

International Search Report and Written Opinion in connection with PCT/US2009/058265 dated Apr. 28, 2010, 7 pages.

(Continued)

*Primary Examiner* — Nicholas Woodall
(74) *Attorney, Agent, or Firm* — Fliesler Meyer LLP (57) ABSTRACT

A system adapted to be implanted in a patient to stabilize a spinal column of the patient comprises an anchoring plate having a shape generally conformal with at least a portion of a lamina associated with a targeted vertebra of the spinal column. The anchoring plate is securable to the targeted vertebra by two or more screws. A mounting bracket adapted to receive an secure a rod is connected with the anchoring plate.

19 Claims, 7 Drawing Sheets

(56) References Cited

U.S. PATENT DOCUMENTS

| | | |
|---|---|---|
| 6,152,927 A | 11/2000 | Farris et al. |
| 6,193,721 B1 | 2/2001 | Michelson |
| 6,197,028 B1 | 3/2001 | Ray et al. |
| 6,224,602 B1 | 5/2001 | Hayes |
| 6,293,949 B1 | 9/2001 | Justis et al. |
| 6,306,136 B1 | 10/2001 | Baccelli |
| 6,383,186 B1 | 5/2002 | Michelson |
| 6,398,783 B1 | 6/2002 | Michelson |
| 6,402,756 B1 | 6/2002 | Ralph et al. |
| 6,428,542 B1 | 8/2002 | Michelson |
| 6,454,771 B1 | 9/2002 | Michelson |
| 6,520,990 B1 | 2/2003 | Ray |
| 6,527,776 B1 | 3/2003 | Michelson |
| 6,565,570 B2 | 5/2003 | Sterett et al. |
| 6,565,605 B2 | 5/2003 | Goble et al. |
| 6,579,290 B1 | 6/2003 | Hardcastle et al. |
| 6,592,586 B1 | 7/2003 | Michelson |
| 6,610,091 B1 | 8/2003 | Reiley |
| 6,620,163 B1 | 9/2003 | Michelson |
| 6,811,567 B2 | 11/2004 | Reiley |
| 6,936,050 B2 | 8/2005 | Michelson |
| 6,936,051 B2 | 8/2005 | Michelson |
| 6,949,123 B2 | 9/2005 | Reiley |
| 6,969,390 B2 | 11/2005 | Michelson |
| 7,041,105 B2 | 5/2006 | Michelson |
| 7,044,952 B2 | 5/2006 | Michelson |
| 7,048,736 B2 | 5/2006 | Robinson et al. |
| 7,074,237 B2 | 7/2006 | Goble et al. |
| 7,077,844 B2 | 7/2006 | Michelson |
| 7,087,084 B2 | 8/2006 | Reiley |
| 7,090,698 B2 | 8/2006 | Goble et al. |
| 7,097,645 B2 | 8/2006 | Michelson |
| 7,112,202 B2 | 9/2006 | Michelson |
| 7,115,130 B2 | 10/2006 | Michelson |
| 7,186,256 B2 | 3/2007 | Michelson |
| 7,232,441 B2 | 6/2007 | Altarac et al. |
| 7,399,301 B2 | 7/2008 | Michelson |
| 7,651,497 B2 | 1/2010 | Michelson |
| 2002/0128655 A1 | 9/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0040746 A1 | 2/2003 | Mitchell et al. |
| 2003/0060828 A1 | 3/2003 | Michelson |
| 2003/0181912 A1 | 9/2003 | Michelson |
| 2004/0006391 A1 | 1/2004 | Reiley |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0111154 A1 | 6/2004 | Reiley |
| 2004/0162558 A1 | 8/2004 | Hegde et al. |
| 2004/0181222 A1* | 9/2004 | Culbert et al. .................. 606/60 |
| 2004/0181226 A1 | 9/2004 | Michelson |
| 2004/0181229 A1 | 9/2004 | Michelson |
| 2004/0186476 A1 | 9/2004 | Michelson |
| 2004/0236334 A1 | 11/2004 | Michelson |
| 2004/0236335 A1 | 11/2004 | Michelson |
| 2005/0027297 A1 | 2/2005 | Michelson |
| 2005/0027298 A1 | 2/2005 | Michelson |
| 2005/0165400 A1* | 7/2005 | Fernandez ...................... 606/69 |
| 2006/0229610 A1* | 10/2006 | Piehl .............................. 606/61 |
| 2007/0233119 A1 | 10/2007 | Markworth |
| 2009/0125067 A1* | 5/2009 | Mazzuca et al. .............. 606/280 |

FOREIGN PATENT DOCUMENTS

| | | |
|---|---|---|
| WO | 94/26193 | 11/1994 |
| WO | 95/35067 | 12/1995 |
| WO | 96/08206 | 3/1996 |
| WO | 99/56653 | 11/1999 |
| WO | 01/26566 | 4/2001 |
| WO | 2005034722 A2 | 4/2005 |

OTHER PUBLICATIONS

"Spinal Injuries," Rod and Smith's Operative Surgery—Orthopedics Part 1, ed. Hugh A.F. Dudley, ed. David C. Carter, ed. R.C.G. Russell, London: Butterworth-Heinemann, 1991, pp. 637-641.

Heller, John G., et al., "Post-Laminectomy Instability of the Cervical Spine: Etiology and Stabilization Technique," The Adult Spine: Principles and Practice, vol. 2, ed. J.W. Frymoyer, New York: Raven Press, Ltd., 1991, pp. 1219-1240.

Krag, Martin H., "Biomechanics of the Cervical Spine: Internal Fixation," The Adult Spine: Principles and Practice, vol. 1, 2nd edition, ed. J.W. Frymoyer, Philadelphia: Lippincott-Raven Publishers, 1996, pp. 1096-1109.

Extended European Search Report dated Apr. 15, 2013 for Application No. 09816868.5 / PCT/US2009/058265, 7 pages.

* cited by examiner

SYSTEM AND METHOD TO STABLIZE A SPINAL COLUMN INCLUDING A SPINOLAMINAR LOCKING PLATE

CLAIM TO PRIORITY

This application claims priority to U.S. Provisional Application No. 61/194,516, filed Sep. 29, 2008, entitled "SPINOLAMINAR LOCKING PLATE UTILIZING ANATOMIC PRE-CONTOURED DESIGN AND LOCKING", incorporated herein by reference.

TECHNICAL FIELD

Embodiments of the present invention relate to systems and methods to stabilize a spinal column.

BACKGROUND OF INVENTION

Degenerative changes of the spinal column are the most common underlying cause of chronic back pain. The peak incidence of symptoms occurs between the ages of 30 and 50, a period of life during which the most strenuous job and sports-related activities occur. As individuals age, degenerative changes accumulate, affecting the vertebral discs, vertebra, facet joints, and ligaments in the thoracic and lumbar region and can lead to compression of spinal nerves and spinal nerve roots.

It can be desirable to reduce the compression of spinal nerves and spinal nerves by stabilizing the spinal column. The spinal column can be stabilized by isolating spinal motion segment and restricting relative motion between adjacent vertebrae. Alternatively, when conservative treatment fails to control the pain of degenerative disc disease, stenosis and spondylolisthesis, a common surgical approach is spinal fusion; over 200,000 spinal fusions are performed each year. The disc and other material that may be compressing nerve roots are removed and the vertebrae superior and inferior to the removed disc are fused. During the fusion process it is also desirable to restrict relative motion between vertebrae undergoing fusion while bone grows and fusion is complete.

DETAILED DESCRIPTION OF THE PREFERRED EMBODIMENTS

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears. Reference numerals used in a drawing may or may not be referenced in the detailed description specific to such drawing if the associated element is described elsewhere. Further, the terms "vertical" and "horizontal" are used throughout the detailed description to describe general orientation of structures relative to the spine of a human patient that is standing.

The disclosed systems and methods of the present invention generally relate to systems and methods to stabilize a spinal column. In an embodiment of an invention, a spinolaminar locking plate includes a pre-contoured anatomical plate utilizing locking screws for posterior stabilization of the thoracolumbar spine. The disclosed systems and methods of the present invention may also be used with systems and methods to restrict relative motion of vertebral segments for example to assist in spinal fusion procedures.

Figure 1:
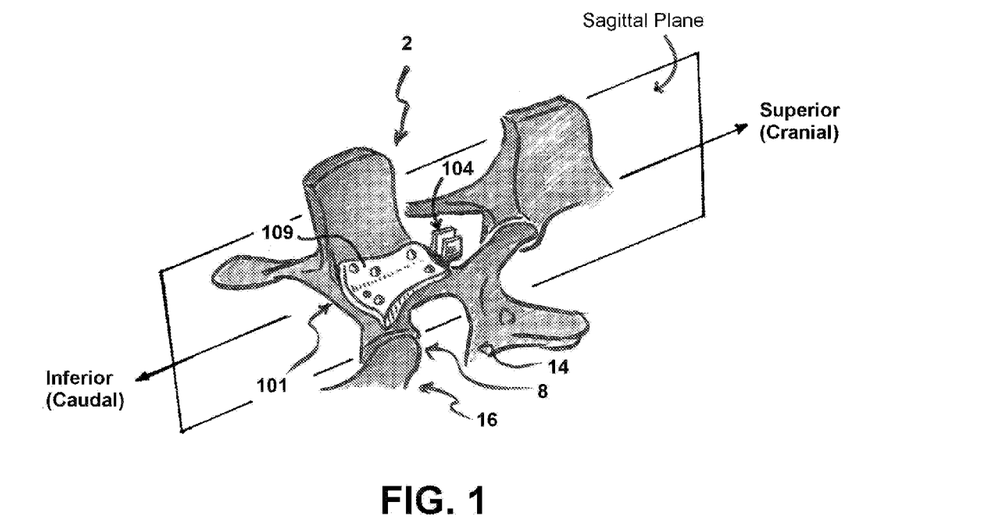
FIG. 1 is a perspective posterior view of an embodiment of an anchoring plate and mounting bracket for use in a system to stabilize a spinal column in accordance with the present invention, the anchoring plate being positioned at an implantation site along the thoracolumbar region of the spinal column.

FIG. 1 is a perspective posterior view of an embodiment of an anchoring plate 101 for use in a system and method to stabilize a spinal column in accordance with the present invention. The anchoring plate 101 has a shape that is generally conformal with the outer surface of the targeted vertebra and generally spans the surface of the lamina (obscured by the anchoring plate 101 in FIG. 1) from near a location where the pedicle 14 joins the lamina to a location near where the lamina joins the spinous process 2. Optionally, the anchoring plate 101 can extend to the inferior articular process 8 of the targeted vertebra. The shape of the anchoring plate 101 allows the anchoring plate 101 to span multiple structures of the vertebra while being generally confined to the surface of the vertebra. The shape of the anchoring plate 101 further allows the anchoring plate 101 to be secured to the structures so that a load applied to the anchoring plate 101 during extension motion and flexion motion of the spinal column is distributed across the multiple structures to reduce a concentration of compressive or tensile force. Reducing compressive or tensile force can be particularly useful where the bone of one or more of the structures has degenerated or otherwise been weakened, for example in osteoporotic patients. The anchoring plate 101 includes a mounting bracket 104 extending therefrom. The mounting bracket 104 in the embodiment extends about perpendicular to the anchoring plate 101 and is fixed relative to the anchoring plate 101. In the embodiment the mounting bracket 104 extends from the superior (cranial) end of the anchoring plate 101. In other embodiments the bracket can extend from the inferior (caudal) end of the anchoring plate 101. Still alternatively, the mounting bracket 104 can extend from any position on the upper surface 109 of the anchoring plate 101. Additionally the mounting bracket 104 can mounted so that it may move such as by rotation relative to the anchoring plate 101. As shown, the anchoring plate 101 is positioned to be secured to the vertebra at structures to the right of the spinous process 2; however, as described in more detail below, additional or alternative implantation sites can be located at structures to the left of the spinous process 2.

Figure 2A:
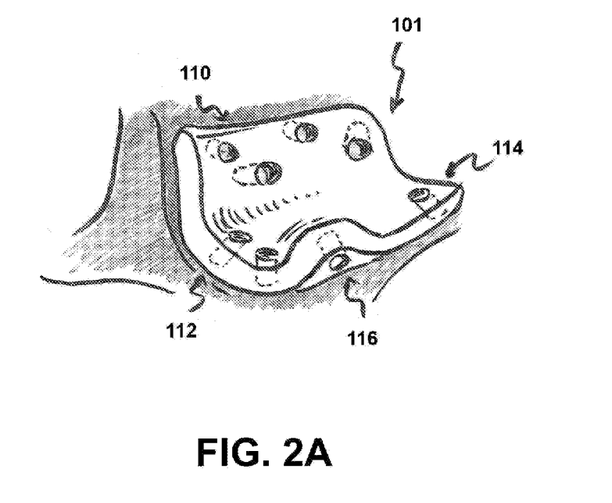
FIG. 2A is a perspective posterior view of an alternative embodiment of an anchoring plate for use in a system to stabilize a spinal column in accordance with the present invention, the anchoring plate being positioned at an implantation site.

Referring to FIG. 2A, a detailed view of the anchoring plate 101 is shown. The anchoring plate 101 includes multiple through-holes for receiving bone screws to secure the anchoring plate to multiple structures. As shown in FIG. 2A (which includes through-holes that vary slightly in arrangement from FIG. 1) there are four through-holes 110 exposing the spinous process 2 at or above where the lamina joins the spinous process (i.e., the spinolaminar junction), two through-holes 112 exposing the lamina, a through-hole 114 exposing a location where the lamina joins the pedicle, and a through-hole 116 exposing the facet joint where the inferior articular process 8 mates with the superior articular process 16 of a vertebra below the targeted vertebra along the spinal column. The through-holes 110, 112, 114, 116 extend through the anchoring plate 101 at angles appropriate to direct a bone screw to the respective structures so that a shank of a bone screw is oriented at a desired angle relative to the sagittal plane. The bone screw is directed to penetrate and seat within the structure in a predictable fashion. Predictability of implantation reduces the opportunity for damage, for example by reducing the opportunity to penetrate the vertebral foramen and damage nerves when driving a pedicle screw into the pedicle.

Figure 2B:
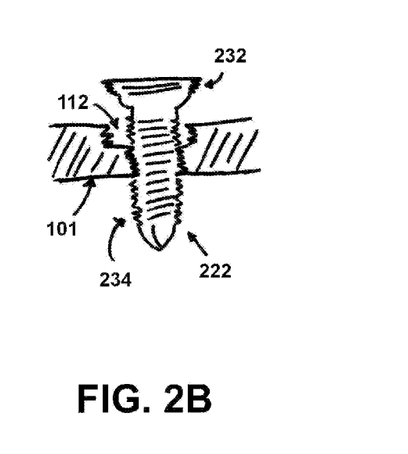
FIG. 2B is a cross-section of a bone screw for use with systems and methods of the present invention partially seated within a threaded hole.

In preferred embodiments, the through-holes can be threaded so as to engage the threads of the shank and further restrict the range of angles at which the bone screw penetrates and seats within the structure, increasing the precision of the trajectory of the bone screw as it seats within the bone. Optionally, one or more of the bone screws can be a locking screw that includes a threaded head to resist backing out of a seated position in the through-holes. FIG. 2B is a cross-section of a locking screw 222 partially seated at the lamina. The threads of the shank 234 engage complementary threads of the through-hole 112. A portion of the through-hole 112 includes an expanded diameter that complements finely pitched threads of the head 232 of the locking screw 222. As the locking screw 222 seats within the bone of the lamina, the threads of the head 232 engage the threads of the expanded diameter of the through-hole 112 so that the locking screw 222 resists backing out of the bone. The locking screw 222 can be particularly useful where the bone stock at an implantation site has degenerated or is otherwise of poor quality.

As will be appreciated, the angle of orientation of the shanks of the different bone screws relative to the sagittal plane vary and/or the range of angles of orientation of the shanks of the first, second, and third screws relative to the sagittal plane do not overlap. The splayed arrangement of the bone screw shanks provides improved resistance to pull-out force, thereby, reducing or eliminating the need to notch or remove portions of the bone and/or provide additional hooks or grafted structures.

The inferior articular process 8 of the targeted vertebra and the superior articular process 16 of the vertebra directly below the targeted vertebra along the spinal column mate at the facet joint to guide and limit movement of the spinal motion segment. In the lumbar region, for example, the facet joint prevents rotation in the transverse plane, while allowing sagittal rotation (flexion and extension) and a small amount of frontal rotation (lateral bending). A through-hole 116 of the anchoring plate 101 can direct a facet screw so that the facet screw penetrates and seats within both the superior and inferior facets, restricting all movement at the facet joint to further stabilize the spinal column. Placement of locking facet screws can enhance facet fusion.

Figure 3:
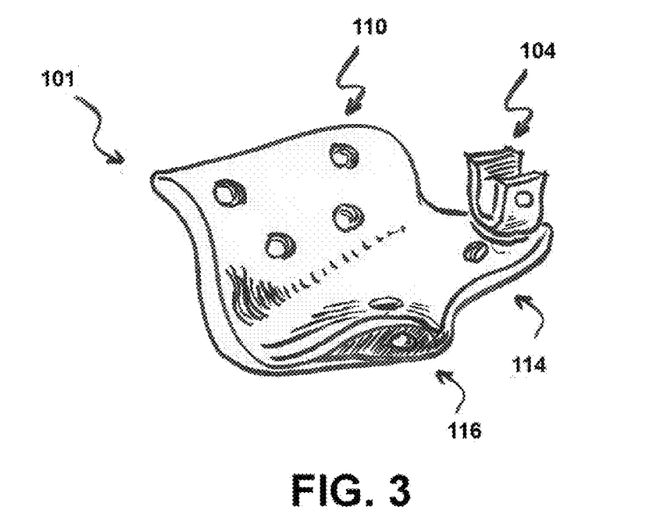
FIG. 3 is an oblique view of an alternative embodiment of an anchoring plate and mounting bracket for use in a system to stabilize a spinal column in accordance with the present invention.
Figure 4:
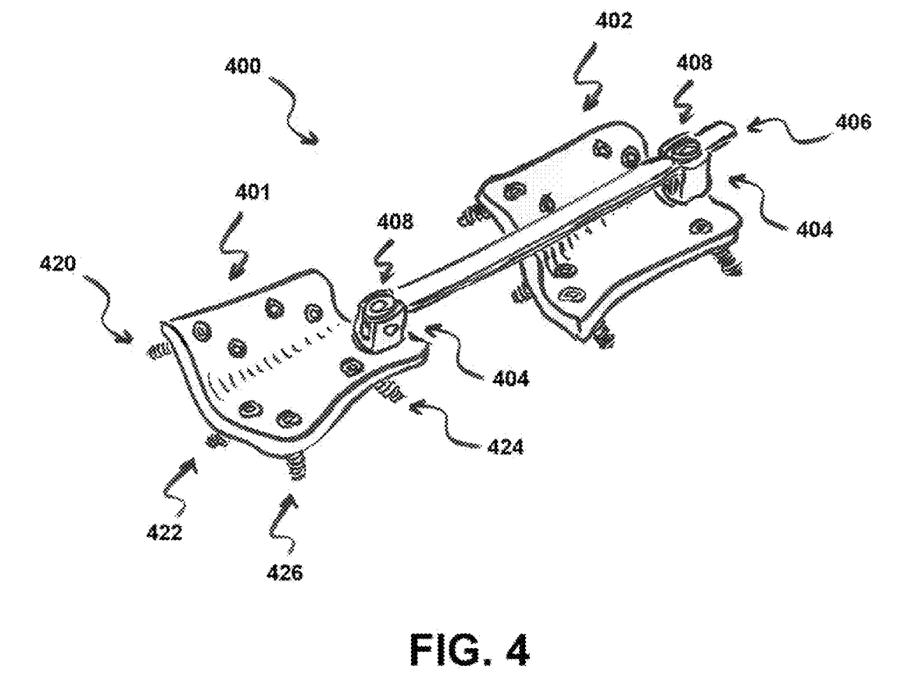
FIG. 4 is an oblique view of an embodiment of a system to stabilize a spinal column in accordance with the present invention by restricting relative movement between two vertebral bodies.

FIG. 3 is an oblique view of the anchor plate 101 illustrating a mounting bracket 104 that extends from the anchoring plate (as shown in FIG. 1, but removed in FIG. 2A). The mounting bracket 104 can be fixedly connected with the anchoring plate 110, or alternatively the mounting bracket 104 can be removably attached to the anchoring plate 110, for example by way of a screw thread that engages threads of a mount point on the anchoring plate 110. Additionally an anchoring plate 101 can have multiple mounting points, so that the bracket can be selectively located in various positions on the anchoring plate. Further with multiple mounting points, multiple brackets can be mounted on one anchoring plate. By including a mount point separated from the mounting bracket 104, the surgeon can select a mounting bracket 104 appropriate for the procedure. For example, if the procedure isolates multiple spinal motion segments, a surgeon can choose to connect a mounting bracket for the middle vertebra that is adapted to grip a single rod spanning all three vertebrae, or the surgeon can choose a mounting bracket for the middle vertebra that is adapted to grip two rods independently, each rod spanning two adjacent vertebrae. As shown, the mounting bracket 104 includes a polyaxial head resembling the head of a polyaxial screw. Referring briefly to FIG. 4, a rod positioned within the saddle of the mounting bracket can be held in place by a locking set screw mated with threads of the polyaxial head. In other embodiments, the mounting bracket 104 can be some other structure, such as a clamp. One of ordinary skill in the art upon reflecting on the teachings providing herein will appreciate the myriad different techniques and geometries with which mounting brackets for gripping a rod can applied to secure the rod to the anchoring plate.

FIG. 4 is an oblique view of an embodiment of a system 400 to stabilize a spinal column in accordance with the present invention by restricting relative motion at a spinal motion segment. The system includes a first anchoring plate 401 and second anchoring plate 402 each resembling the anchor plates 101 described above with reference to FIGS.

1-3. The anchoring plates 401, 402 are pre-contoured to generally conform to the outer surface of the corresponding targeted vertebra and generally span the surface of the lamina. Generally speaking, anatomic shapes of vertebrae vary by level, between the sexes and between adolescents and adults. Pre-contoured adapter plates can be designed and shaped for all seventeen thoracolumbar vertebrae, for four categories (adult male, adolescent male, adult female, adolescent female). Alternatively, anchoring plates can be customized based on a given patient's anatomy.

As shown, the anchoring plates 401, 402 include four threaded holes to guide bone screws 420 into the base of the spinous process, at or above the spinolaminar junction, a threaded hole to guide a bone screw 422 into the lamina, a threaded hole to guide a pedicle screw 424 into the pedicle and a threaded hole to guide a bone screw 426 into the lamina and/or inferior articular process. It is noted that in the embodiment of FIG. 4, the anchoring plate 401 is not shaped to direct a bone screw through a facet joint. Mounting brackets 404 extend from the anchoring plates 401, 402 and rigidly secure a rod 406 between the mounting brackets 404 using locking set screws 408, preventing relative motion between the adjacent vertebrae. Where desired, additional adjacent spinal motion segments can be stabilized by rigidly connecting three or more levels of vertebrae. As described above a single rod can span multiple levels, or each spinal motion segment can be isolated with separate rods.

Figure 5:
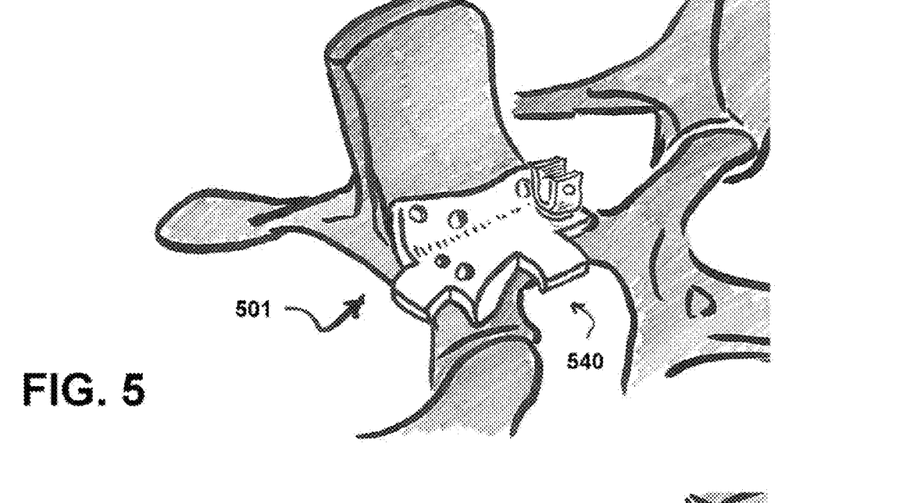
FIG. 5 is a perspective posterior view of a further embodiment of an anchoring plate for use in a system to stabilize a spinal column in accordance with the present invention, the anchoring plate being positioned at an implantation site by way of registration features.
Figure 6:
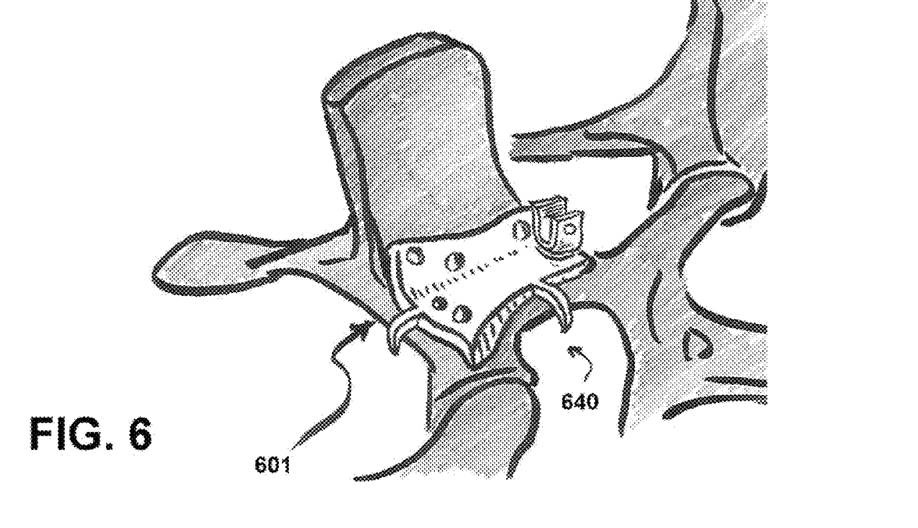
FIG. 6 is a perspective posterior view of a further embodiment of an anchoring plate for use in a system to stabilize a spinal column in accordance with the present invention, the anchoring plate being positioned at an implantation site.

FIGS. 5 and 6 illustrate alternative embodiments of anchor plates in accordance with the present invention. The anchor plate 501 of FIG. 5 includes curved guides 540 that follow the rounded contour of the edges of the lamina, approaching or abutting the ligamenta flava. The curved guides 540 act as registration features and allow the surgeon to precisely position the anchoring plate 501 during implantation to provide addition precision when implanting bone screws. The anchor plate 601 of FIG. 6 includes hooks 640 that pierce and/or distract and/or curve around the ligamenta flava to also act as registration features to allow the surgeon to precisely position the anchoring plate 601 during implantation with very little movement of the anchoring plate 601 to provide addition precision when implanting bone screws.

Figure 7:
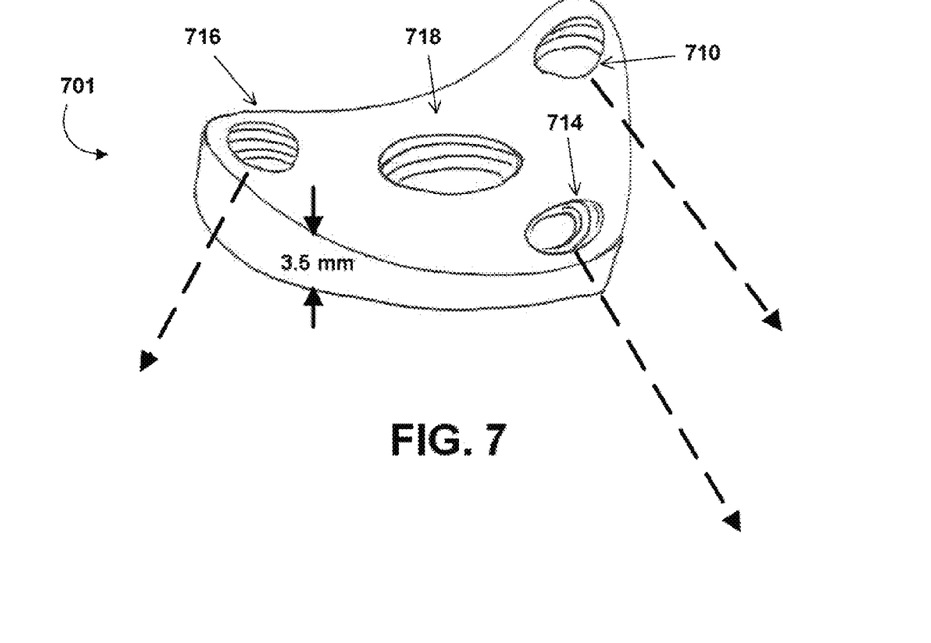
FIG. 7 is an oblique view of a further embodiment of an anchoring plate for use in a system to stabilize a spinal column in accordance with the present invention.
Figure 8:
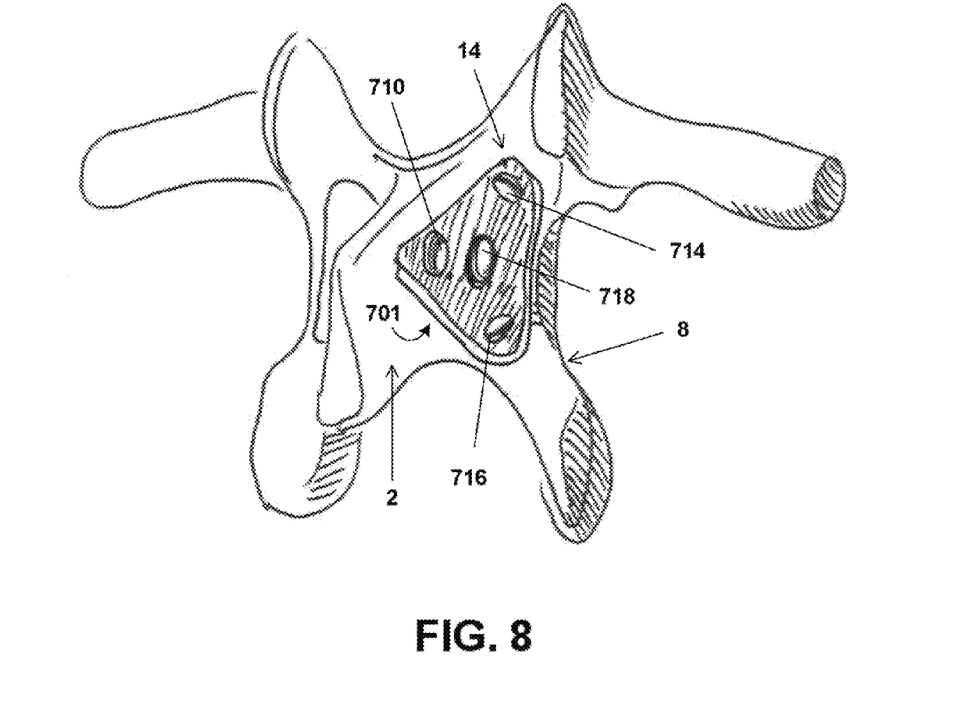
FIG. 8 is perspective posterior view of the anchoring plate of FIG. 7 positioned for attachment to a targeted vertebra.

FIGS. 7 and 8 illustrate a further embodiment of an anchoring plate 701 in accordance with the present invention having a generally triangular shape and comprising three threaded holes 710, 714, 716 for securing the anchoring plate 701 to a targeted vertebra and a center threaded hole for receiving a mounting bracket (not shown). The anchoring plate 701 is shaped to be secured to structures of the vertebra generally to the right of the spinous process 2. As shown, the anchoring plate 701 can have a typical thickness of about 3.5 mm. Phantom lines in FIG. 7 illustrate the trajectory to which bone screws will be guided by threaded holes 710, 714, 716 of the anchoring plate 701. A first threaded hole 710 is formed to guide a bone screw into the base of the spinous process 2 roughly at a junction of the lamina (obscured by the anchoring plate) and spinous process 2. A second threaded hole 716 is formed to guide a bone screw into the inferior articular process 8 of the targeted vertebra and optionally into the superior articular process of a vertebra inferior to the targeted vertebra (not shown). A third threaded hole 714 is formed to guide a bone screw into the pedicle 14 of the targeted vertebra. Before, during or after the anchoring plate 701 has been secured, a mounting bracket (not shown) can be mated with the anchoring plate at a mounting point 718. The mounting bracket can include, for example, a polyaxial head, a rotatable head, or some other structure for securing a rod.

It is noted that, the anchoring plate 701 of FIGS. 7 and 8 includes fewer threaded holes relative to previously described embodiments, overlapping a reduced surface area of the targeted vertebra. As will be appreciated, an anchoring plate can be selected by a surgeon in accordance with the patient's needs. For example, if a patient is osteoporotic or otherwise has poor bone purchase across the targeted vertebral structures, a surgeon may desire to select an anchoring plate as shown in FIGS. 1-3. Still further, the surgeon may decide not to fuse the spinal motion segment at the facet joint, thereby selecting an anchoring plate as shown in FIG. 4. A patient may have generally healthy bone structure; therefore a surgeon may desire to select an anchoring plate as shown in FIGS. 7 and 8. Further, a surgeon can combine different sizes and/or shapes where multiple anchoring plates are used to isolate one or more spinal motion segments. One of ordinary skill in the art, upon reflecting on the teachings contained herein, will appreciate the myriad different shapes and sizes of anchoring plates in accordance with the present invention and/or techniques for selecting appropriate anchoring plates for use in embodiments of method to stabilize a spinal column in accordance with the present invention.

Figure 9:
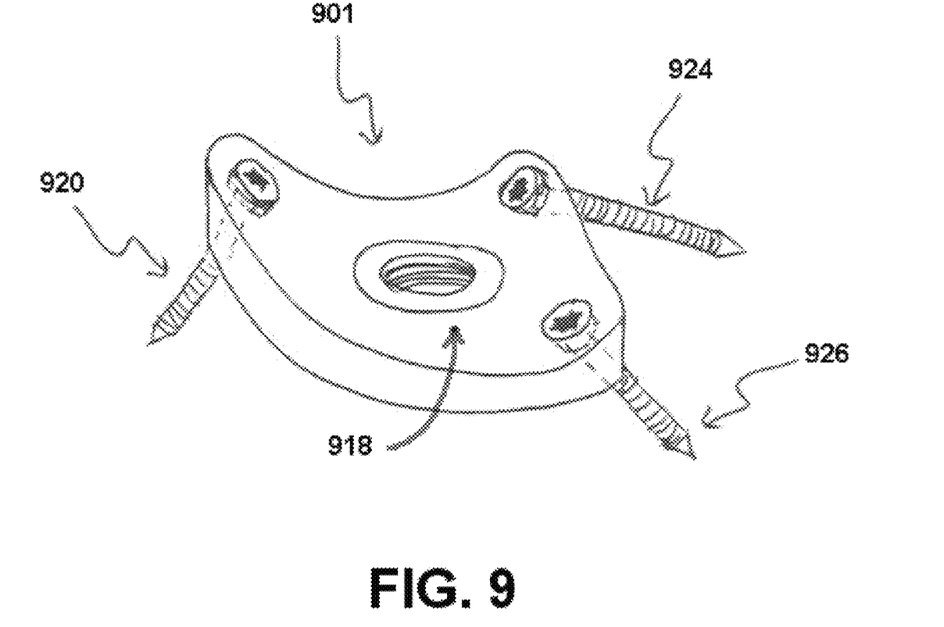
FIG. 9 is an oblique view of a further embodiment of an anchoring plate for use in a system to stabilize a spinal column in accordance with the present invention.

FIG. 9 illustrates a triangular shaped anchoring plate 901 similar to the anchoring plate 701 of FIG. 7, partially rotated to illustrate curvature of the anchoring plate generally conforming with the curvature of the spinolaminar junction of the targeted vertebra. Bone screws 920, 924, 926 are shown seated within threaded holes of the anchoring plate 901. The angle of orientation of the shanks of the bone screws 920, 924, 926 relative to the sagittal plane (shown in FIG. 1) vary and/or the range of angles of orientation of the shanks of the first, second, and third screws relative to the sagittal plane do not overlap. As noted above, the splayed configuration of the bone screws distribute loads applied to a mounting bracket mated with the anchoring plate 901 at a mounting point 918 across selected structures of the targeted vertebra.

Figure 10:
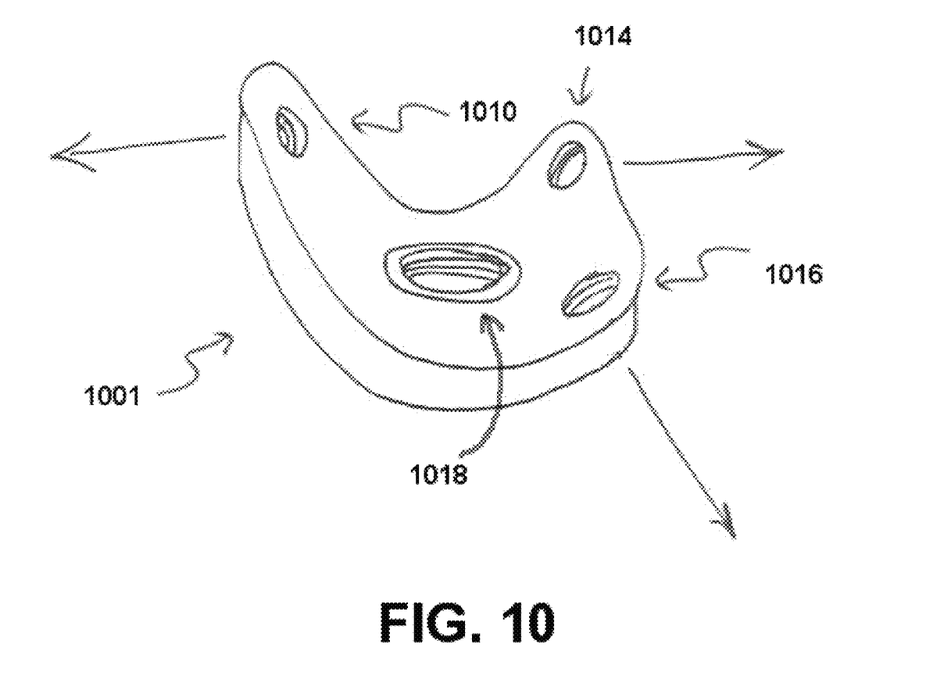
FIG. 10 is an oblique view of a further embodiment of an anchoring plate for use in a system to stabilize a spinal column in accordance with the present invention.

FIG. 10 illustrates a triangular shaped anchoring plate 1001 similar to the anchoring plate 901 of FIG. 9, illustrating more aggressive curvature of the anchoring plate generally conforming with the curvature of the spinolaminar junction of the targeted vertebra. The anchoring plate 1001 includes threaded holes 1010, 1014, 1016 adapted to guide bone screws along trajectories to the structures describe above. As above, the anchoring plate 1001 includes a mounting point 1018, although in other embodiments a mounting bracket (not shown) can be fixedly attached to the anchoring plate or integrally formed with the anchoring plate. As will be appreciated, the shape of the anchoring plate can be made conformal with an outer surface of the targeted vertebra based on myriad different variables, for example the level of the vertebra targeted, the sex of the patient, or alternatively the specific anatomical shape of the targeted vertebra based on imaging (i.e., customized).

Figure 11:
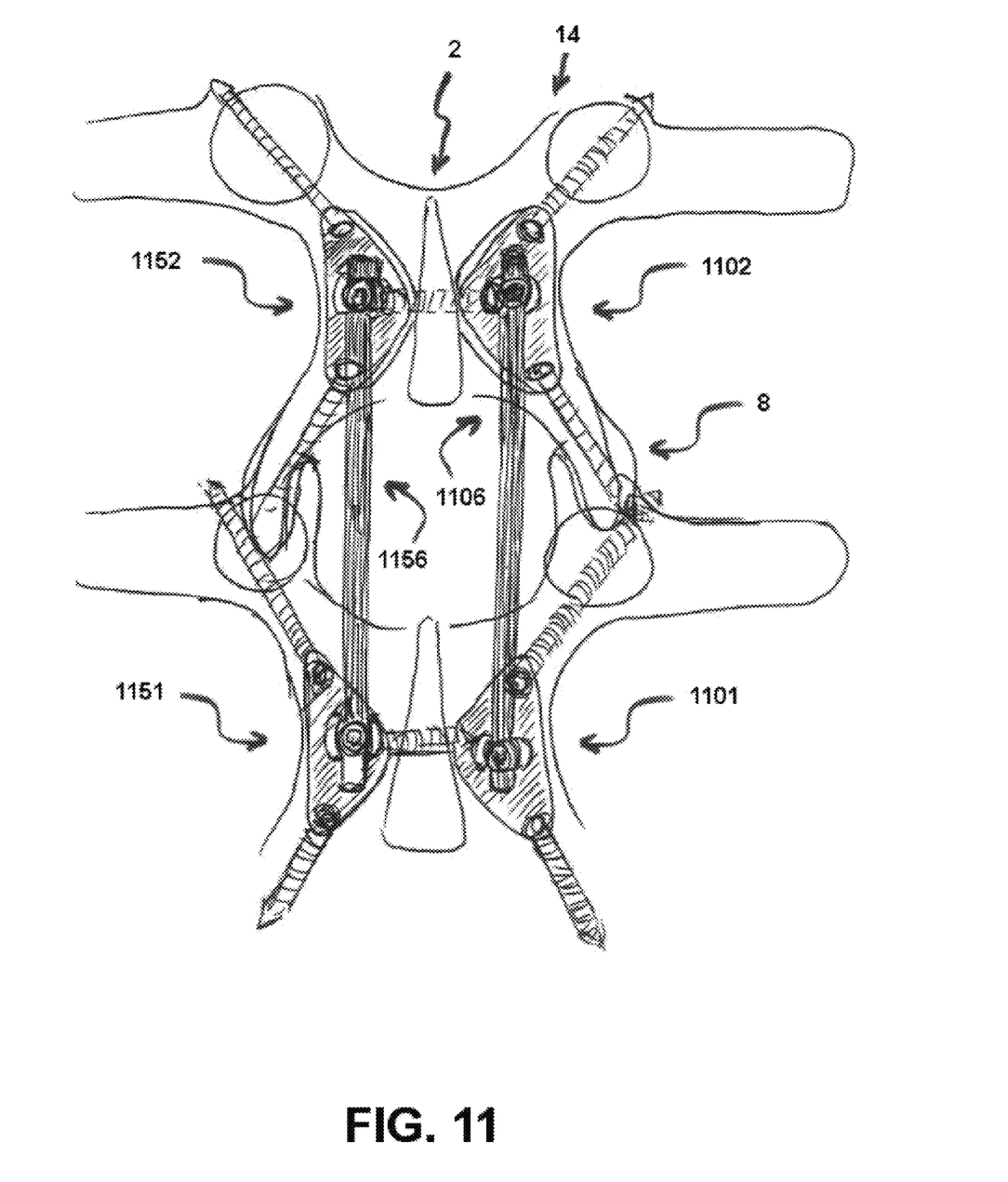
FIG. 11 is a posterior view of an embodiment of a system in accordance with the present invention comprising four anchoring plates for resisting relative motion at a spinal motion segment.

Referring to FIG. 11, an embodiment of a system in accordance with the present invention comprising four anchoring plates 1101, 1102, 1151, 1152 for resisting relative motion at a spinal motion segment is shown. The anchoring plates 1101, 1102, 1151, 1152 are each secured to structures of the respective targeted vertebras as described above (e.g., the spinous process 2, the inferior articular process 8, and the pedicle 14). Relative motion is resisted by mounting a right rod 1106 between two anchoring plates 1101, 1102 secured along the right side of the targeted vertebrae and mounting a left rod 1156 between two anchoring plates 1151, 1152 secured along the left side of the targeted vertebrae.

Figure 12:
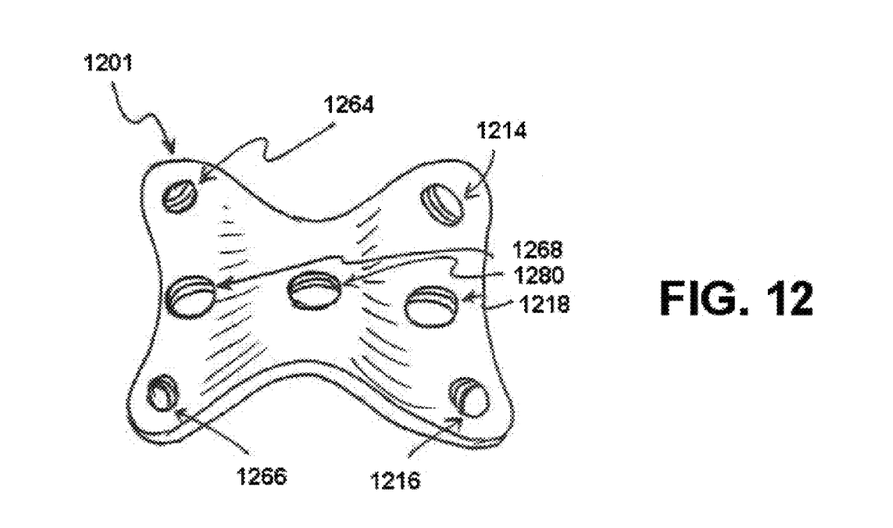
FIG. 12 illustrates a further embodiment of an anchoring plate for use in a system to stabilize a spinal column in accordance with the present invention, the anchoring plate supplanting a spinous process and being anchored to structures on both sides of a vertebra.
Figure 13:
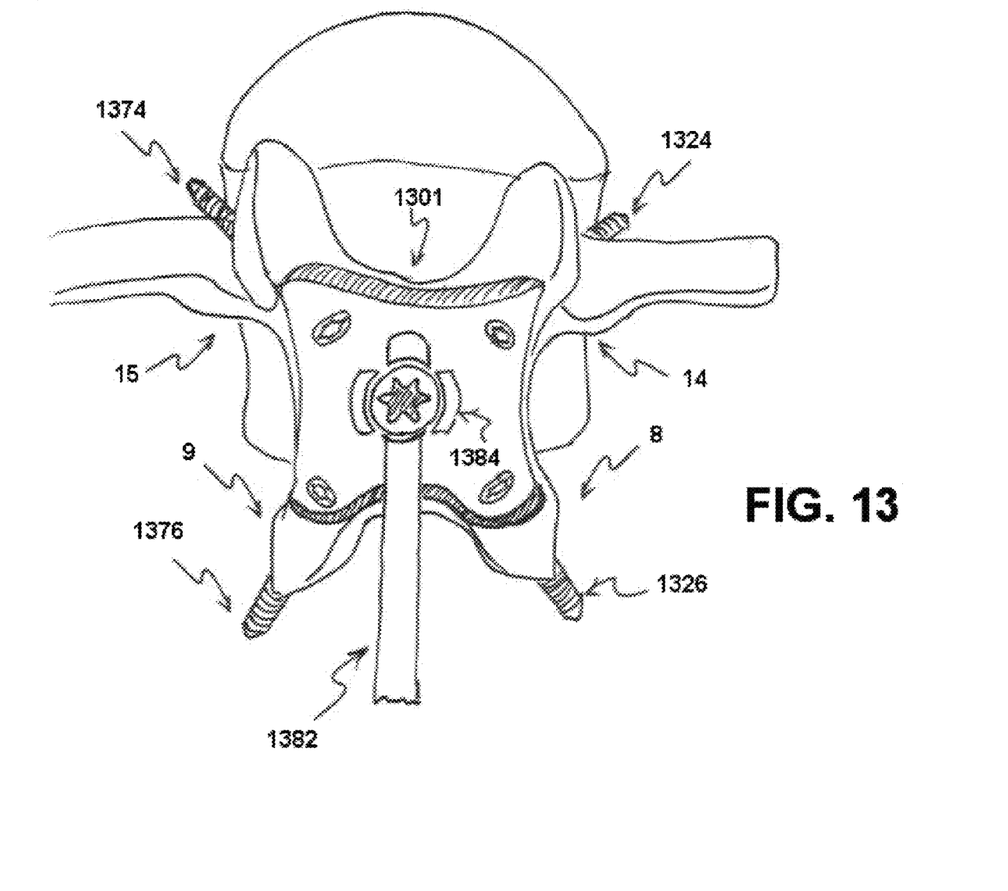
FIG. 13 is a posterior view of the anchoring plate of FIG. 12 positioned at an implantation site.

FIGS. 12 and 13 illustrate further embodiments of anchoring plates 1201, 1301 for use in a system to stabilize a spinal column in accordance with the present invention. The anchoring plate 1201, 1301 are shaped such that they resemble a butterfly with threaded holes 1214, 1216, 1264, 1266 exposing portions of the target vertebra on both sides of the spinous process for securing the anchoring plate 1201, 1301. Use of the anchoring plate 1201 requires removing the spinous process associated with the targeted vertebra. Threaded holes 1216, 1266 at an inferior end of the anchoring plate 1201, 1301 guide bone screws 1326, 1376 along a trajectory seating the bone screws 1326, 1376 into the inferior articular processes 8, 9 and facet joints of the target vertebra. Threaded holes 1214, 1264 at the superior end of the anchoring plate 1201, 1301 guide bone screws 1324, 1374 along a trajectory seating the bone screws into the pedicles 14, 15 of the target vertebra. As shown in FIG. 13, a centrally-located mounting bracket 1384 extends from and is either removably or fixedly connected with the anchoring plate 1301. The mounting bracket 1384 is generally aligned with the removed spinous process and secures a rod 1382 spanning the distance of one or more spinal motion segments from the superior targeted vertebra to one or more inferior targeted vertebra (not shown).

FIG. 12 differs from FIG. 13 in that additional mounting points 1218, 1268 are provided in addition to a mounting point 1280 for connecting a mounting bracket. As described above, mounting brackets can be removably connected with the additional mounting points 1218, 1268 to supplement a centrally-located mounting bracket or in substitution of a centrally-located mounting bracket, or alternatively, the mounting points 1218, 1268, 1280 can be used to secure rods spanning different spinal motion segments (e.g., the outer mounting points can be used to connect mounting brackets connecting the anchoring plate 1301 with mounting brackets (not shown) secured to an anchoring plate at a vertebra superior to the targeted vertebra. Alternatively, the anchoring plate 1201 can include still additional mounting points for securing additional mounting brackets. One of ordinary skill in the art will appreciate, upon reflecting on the teachings herein, the myriad different arrangements of mounting points and mounting brackets that can be associated with an anchoring plate to secure rods spanning one or more additional vertebra superior and inferior to the target vertebra.

The pre-contoured design of the anchoring plates described above ease placement by providing complementary shapes that conform to the generally more easily accessible structures of a given vertebra. Further, the area of the lateral pars (14 in FIG. 1) and the intertransverse interval is free of hardware, providing more area for fusion and bone grafting. The anchoring plates further simplify securing the anchoring plate by providing targeted screw placement. The use of multiple structures can further allow a surgeon to avoid damaged structures. For example, a surgeon may avoid placing hardware (such as pedicle screws) into a site of infection such as the anterior and middle columns for a patient with vertebral spondylodiskitis. The surgeon can further avoid compromised pedicles (type D pedicles, pedicle fracture, intra-operative breach or previous surgery) and primary or metastatic tumors of the vertebral body. The anchor plates can also be used concomitantly with pedicle screws for increased construct rigidity (for instance, in short-segment posterior fusion for burst fractures)

Preferably, the anchoring plate 101 is made of titanium. However, other biocompatible materials such as stainless steel and/or PEEK and/or other related polymers can be used. As will be appreciated upon reflecting on the different embodiments, the structures described herein can vary in size and shape based on factors such as material of construction, anatomical structure of the implantation site, implantation technique and targeted system performance (e.g., stiffness).

Embodiments of systems and methods in accordance with the present invention include an anatomically contoured plate for posterior fixation of the thoracolumbar spine. In at least one embodiment, the system includes:

The anatomically contoured plate placed over the lamina of a vertebra from the spinolaminar junction medially to the facet laterally.

The plate having threaded holes to accommodate locking screws (having diameters, for example, of 3.5 and 4.0 mm).

The screw heads lockable onto the plate and providing a fixed-angle construct and high resistance to pullout. Alternatively, in cases of good bone stock, regular non-locking screws may be used.

The screw holes directed towards sites selected from the following areas that generally have good bone stock for screw purchase and allow a generally safe trajectory during screw implantation: the base of the spinous process, the ipsilateral facet joint, the inferior part of the lamina (optional, depending on the lamina thickness), and the ipsilateral pedicle (optional).

The threaded holes acting as drill guides to provide for the precise trajectory of screw placement.

A mounting bracket including a polyaxial saddle (similar to a polyaxial pedicle screw) fixed to the plate to secure a rod, the rod being connectable between two or more levels.

Embodiments of systems and methods in accordance with the present invention may be beneficial in one or more of:

osteoporotic patients with decreased pullout strength of the pedicle screws, patients having vertebral spondylodiscitis, where hardware (e.g., pedicle screw) installation into a site of infection should be avoided, patients having primary or metastatic tumors of the vertebral body, and patients with compromised pedicles (e.g., type D pedicles, pedicle fracture, intra-operative breach or previous surgery).

Embodiments of systems and methods in accordance with the present invention can provide advantages including one or more of:

ease of placement due to pre-contoured design and targeted screw placement, increased area for fusion and bone grafting due to one or more areas of the facet, lateral pars and intertransverse interval being free of hardware, enhanced facet fusion due to placement of locking facet screws, and the possibility of concomitant use of pedicle screws for increased construct rigidity (for instance, in short-segment posterior fusion for burst fractures).

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

The invention claimed is:

1. A system adapted to be implanted in a patient to stabilize a spinal column of the patient comprising:
a single-member anchoring plate having an anatomically pre-contoured shape conformal with one of a left or a right lamina of the spinous process of a targeted vertebra of the spinal column, the anchoring plate including:
a first threaded hole to receive a first screw having a shank and a head, the first threaded hole adapted to direct the first screw into a spinous process associated with the targeted vertebra and restrict orientation of the shank to a first angle and/or range of angles relative to the sagittal plane while the first screw is advanced along the first threaded hole;
a second threaded hole to receive a second screw having a shank and a head, the second threaded hole adapted to direct the second screw into a facet joint associated with the targeted vertebra and restrict orientation of the shank to a second angle and/or range of angles relative to the sagittal plane while the second screw is advanced along the second threaded hole;
a third threaded hole to receive a third screw having a shank and a head, the third threaded hole adapted to direct the third screw into a pedicle associated with the targeted vertebra and restrict orientation of the shank to a third angle and/or range of angles relative to the sagittal plane while the third screw is advanced along the third threaded hole;
a mounting point including a fourth hole adapted to receive a mounting bracket, the mounting bracket adapted to receive and secure a rod, and
wherein the first, second and third threaded holes have a non-linear orientation, the non-linear orientation of the threaded holes allows the screws positioned in the first, second and third threaded holes to splay outwardly;
wherein when the first, second, and third screws are received and seated within corresponding screw holes the angle of orientation of the shanks of the first, second, and third screws relative to the sagittal plane vary and/or the range of angles of orientation of the shanks of the first, second, and third screws relative to the sagittal plane do not overlap; and
wherein when the first, second, and third screws are received and seated within corresponding screw holes the shanks of the first, second, and third screws engage at least two different structures of the targeted vertebra.

2. The system of claim 1, further comprising:
a mounting bracket mounted on top of the single-member anchoring plate through the fourth threaded hole.

3. The system of claim 2, wherein the mounting bracket is a polyaxial saddle.

4. The system of claim 2, wherein:
the mounting bracket is disconnectable from the single-member anchoring plate.

5. The system of claim 1, wherein the single-member anchoring plate is fabricated from at least one of stainless steel, titanium, PEEK or some other biocompatible material.

6. The system of claim 1, further comprising:
a first screw adapted to penetrate and hold the spinous process;
a second screw adapted to penetrate an inferior articular process of the targeted vertebra and a superior articular process of a vertebra above the targeted vertebra to resist motion at the facet joint; and
a third screw adapted to penetrate and hold the pedicle or the lamina.

7. The system of claim 6, wherein:
the head of one or more of the first, second, and third screws is threaded; and
a threaded hole corresponding to the screw having the threaded head includes a primary thread for receiving a thread of the corresponding shank, and a locking thread for receiving the thread of the corresponding head; and
when the screw including the threaded head is seated within the corresponding threaded hole, the screw resists backing out.

8. The system of claim 1, further comprising:
one or more registration features for aligning the single-member anchoring plate to the targeted vertebra so that the generally conformal surface of the single-member anchoring plate is generally matched to the complementary surface of the targeted vertebra.

9. The system of claim 1, wherein the size of the fourth hole is larger than the size of the first, second, or third threaded hole.

10. The system of claim 1, wherein the single-member anchoring plate has a triangle shape.

11. A system adapted to be implanted in a patient to stabilize a spinal column of the patient comprising:
a single-member first left anchoring plate having an anatomically pre-contoured shape conformal with an upper lamina associated with a left side of a superior targeted vertebra of the spinal column;
a first left mounting bracket mounted on top of the first left single-member anchoring plate;
a single-member second left anchoring plate having an anatomically pre-contoured shape generally conformal with a lower lamina associated with a left side of an inferior targeted vertebra of the spinal column;
a second left mounting bracket mounted on top of the second left single-member anchoring plate;
a left rod extending at least between the first mounting bracket and the second mounting bracket, the left rod being secured to the first mounting bracket and the second mounting bracket to resist relative movement between superior and inferior targeted vertebrae;
a single-member first right anchoring plate having an anatomically pre-contoured shape generally conformal with an upper lamina associated with a right side of a superior targeted vertebra of the spinal column;
a first right mounting bracket mounted on top of the first right single-member anchoring plate;
a single-member second right anchoring plate having an anatomically pre-contoured shape generally conformal with a lower lamina associated with a right side of an inferior targeted vertebra of the spinal column;
a second right mounting bracket mounted on top of the second right single-member anchoring plate;
a right rod extending at least between the first right mounting bracket and the second right mounting bracket, the right rod being secured to the first right mounting bracket and the second right mounting bracket to resist relative movement between superior and inferior targeted vertebrae;
wherein each of the single-member anchoring plates further includes
a first threaded hole to receive a first screw having a shank and a head, the first threaded hole adapted to direct the first screw into the superior targeted vertebra and restrict orientation of the shank to a first angle and/or range of angles relative to the sagittal plane while the first screw is advanced along the first threaded hole,
a second threaded hole to receive a second screw having a shank and a head, the second threaded hole adapted to direct the second screw into the superior targeted vertebra and restrict orientation of the shank to a second angle and/or range of angles relative to the sagittal plane while the second screw is advanced along the second threaded hole,
a third threaded hole to receive a third screw having a shank and a head, the third threaded hole adapted to direct the third screw into the superior targeted vertebra and restrict orientation of the shank to a third angle and/or range of angles relative to the sagittal plane while the third screw is advanced along the third threaded hole,
a mounting point including a fourth hole adapted to receive the mounting bracket, and
wherein the first, second and third threaded holes have a non-linear orientation, the non-linear orientation of the threaded holes allows the screws positioned in the first, second and third threaded holes to splay outwardly,
wherein when the first, second, and third screws are received and seated within corresponding screw holes the angle of orientation of the shanks of the first, second, and third screws relative to the sagittal plane vary and/or the range of angles of orientation of the shanks of the first, second, and third screws relative to the sagittal plane do not overlap,
wherein when the first, second, and third screws are received and seated within corresponding screw holes the shanks of the first, second, and third screws engage at least two different structures of the targeted vertebra, and
wherein each of the single-member anchoring plates has a triangle shape.

12. The system of claim 11, wherein each mounting bracket is a polyaxial saddle.

13. The system of claim 11, wherein each single-member anchoring plate is fabricated from at least one of stainless steel, titanium, PEEK or some other biocompatible material.

14. The system of claim 11, wherein:
the first threaded hole is adapted to direct the first screw into a spinous process associated with the targeted vertebra;
the second threaded hole is adapted to direct the second screw into an facet joint associated with the targeted vertebra; and
the third threaded hole is adapted to direct the third screw into a pedicle associated with the targeted vertebra or the lamina associated with the targeted vertebra.

15. The system of claim 11, further comprising for each of the single-member anchoring plates:
a first screw adapted to penetrate and hold the spinous process;
a second screw adapted to penetrate an inferior articular process of the targeted vertebra and a superior articular process of a vertebra above the targeted vertebra to resist motion at the facet joint; and
a third screw adapted to penetrate and hold the pedicle or the lamina.

16. The system of claim 15, wherein:
the head of one or more of the first, second, and third screws is threaded; and
a threaded hole corresponding to the screw having the threaded head includes a primary thread for receiving a thread of the corresponding shank, and a locking thread for receiving the thread of the corresponding head; and
when the screw including the threaded head is seated within the corresponding threaded hole, the screw resists backing out.

17. The system of claim 11, wherein each of the single-member anchoring plates further includes
one or more registration features for aligning the single-member anchoring plate to the corresponding targeted vertebra so that the conformal surface of the single-member anchoring plate is matched to the complementary surface of the corresponding targeted vertebra.

18. A system adapted to be implanted in a patient to stabilize a spinal column of the patient comprising:
a single-member anchoring plate having an anatomically pre-contoured shape conformal with structures of a targeted vertebra of the spinal column including at least a portion of a lamina, at least a portion of an inferior articular, and at least a portion of a spinous process, the single-member anchoring plate including:
at least a first threaded hole adapted to direct a first screw into the spinous process,
at least a second threaded hole adapted to direct a second screw into a pedicle associated with the targeted vertebra,
at least a third threaded hole adapted to direct a third screw into a facet joint including the inferior articular process and a superior articular process associated with a vertebra superior to the targeted vertebra along the spinal column so that motion at the facet joint is restricted, wherein the first, second and third threaded holes have a non-linear orientation, the non-linear orientation of the threaded holes allows the screws positioned in the first, second and third threaded holes to splay outwardly,
at least one mounting point including a fourth hole adapted to receive a mounting bracket, and
a mounting bracket mounted on the single-member anchoring plate and including a polyaxial saddle, the mounting bracket adapted to receive and secure a rod.

19. A system adapted to be implanted in a patient to stabilize a spinal column of the patient comprising:
a single-member anchoring plate having an anatomically pre-contoured shape conformal with structures of a targeted vertebra of the spinal column including at least a portion of a lamina, and at least a portion of a spinous process, the single-member anchoring plate including:
a first threaded hole adapted to direct a first screw into the spinous process,
a second threaded hole adapted to direct a second screw into a pedicle associated with the targeted vertebra,
a third threaded hole adapted to direct a third screw into the lamina; and
a mounting bracket mounted on the single-member anchoring plate and including a polyaxial saddle, the mounting bracket adapted to receive and secure a rod,
wherein the first, second and third threaded holes have a non-linear orientation, the non-linear orientation of the threaded holes allows the screws positioned in the first, second and third threaded holes to splay outwardly.

* * * * *